US00PP20769P2

(12) United States Plant Patent
Knight

(10) Patent No.: US PP20,769 P2
(45) Date of Patent: Feb. 23, 2010

(54) RASPBERRY PLANT NAMED 'AUTUMN TREASURE'

(50) Latin Name: *Rubus idaeus l.*
Varietal Denomination: Autumn Treasure

(75) Inventor: Victoria Hamilton Knight, Maidstone (GB)

(73) Assignee: East Malling Research, East Malling (GB)

( * ) Notice: Subject to any disclaimer, the term of this patent is extended or adjusted under 35 U.S.C. 154(b) by 0 days.

(21) Appl. No.: 12/074,053

(22) Filed: Feb. 29, 2008

(51) Int. Cl.
*A01H 5/00* (2006.01)

(52) U.S. Cl. ..... Plt./204
(58) Field of Classification Search ..... Plt./204
See application file for complete search history.

*Primary Examiner*—Kent L Bell
(74) *Attorney, Agent, or Firm*—Mark P. Bourgeois

(57) ABSTRACT

A new and distinct Raspberry plant named 'Autumn Treasure' is provided that is the product of a controlled breeding program. The new primocane fruiting Raspberry cultivar produces attractive conical-shaped medium red fruit that detaches readily from the receptacle. It crops approximately ten days later than the cultivar 'Autumn Bliss' (U.S. Plant Pat. No. 6,597) in Southern England. The new cultivar has very good plant habit with spineless, erect canes where the fruit is well presented to the pickers. Due to its excellent pest and disease resistance 'Autumn Treasure' is very well suited to low-input systems as well as conventional production.

3 Drawing Sheets

Botanical classification: *Rubus idaeus l.*

Variety denomination: 'Autumn Treasure'.

BACKGROUND OF THE INVENTION

The new cultivar 'Autumn Treasure' was created in the course of the controlled breeding program carried out at East Malling Research (EMR), Kent, United Kingdom in 1995. Two breeding lines from the East Malling breeding programme were chosen as parents and crossed with the aim of combining their desirable characteristics. The female parent (i.e., the seed parent) was the numbered selection 'EM6304/36' (not patented). This was an extremely early summer fruiting selection with a condensed ripening season at East Malling (Kent, UK). The fruit was attractive and with good flavour. The plant was spineless, resistant to biotypes 1–4 of the large raspberry aphid, *Amphorophora idaei*. It had *R. occidentalis, R. crataegifolius* and *R. spectabilis* in its ancestry. The male parent (i.e., the pollen parent) was the numbered selection 'EM6330/96' (not patented). This was a very early primocane fruiting selection which had very high crop potential and good plant growth habit at East Malling (Kent, UK).The plant was spiny and resistant to biotypes 1–4 of the large raspberry aphid, *A. idaei*. It had a very complex ancestry that included *R. occidentalis, R. idaeus strigosus, R. odoratus, R. arcticus, R. crataegifolius* and *R. spectabilis*. Neither of the parents were released as cultivars and no plants of either selection exist any longer.

The seeds resulting from the above pollination were sown and small plants were obtained which were genetically and phenotypically different from each other. Seedlings were selected for spinelessness and *Amphorophora idaei* resistance in the glasshouse and planted in the open field at East Malling in 1996. The new cultivar was selected as a single plant from those seedlings in 1999 and has subsequently been vegetatively propagated in 1999 at East Malling by division of rooted canes, etiolated root cuttings as well as by in vitro shoot tip culture for trialing and testing. 'Autumn Treasure' has a vigorous root system and propagates readily.

SUMMARY OF THE INVENTION

The present invention provides a new and distinct cultivar, named 'Autumn Treasure', of Raspberry plant (*Rubus idaeus l.*). The 'Autumn Treasure' cultivar has been selected for primocane production and crops from the third week of July until the middle of October in the Southeast of England. It reaches 50% pick date in late August to early September, 10 to 14 days later than 'Autumn Bliss' (U.S. Plant Pat. No. 6,597). The canes from 'Autumn Treasure' are spineless and upright; the fruit is produced in short laterals in the top half of the canes, it is well displayed to the pickers and separates easily from its receptacle. The berries are large, long conical and bright in colour and of pleasant flavour. Shelf life of the fruit is of commercial quality, having a low incidence of post-harvest rots from unsprayed trials. This new cultivar is resistant to biotypes 1–4 of the large raspberry aphid (*Amphorophora idaei*), common virus vector in Europe. It is also highly resistant to *Phytophthora* root rot and shows higher tolerance than other cultivars to *Verticillium* wilt. Therefore is well suited, not only to conventional commercial production, but also to low input systems, pick-your-own (U-pick) farms and amateur growers.

BRIEF DESCRIPTION OF THE DRAWINGS

The accompanying photographs show typical specimens of the new cultivar's fruit and plant habit in colour, as nearly true as is reasonably possible to make colour illustrations of these characteristics.

BOTANICAL DESCRIPTION OF THE PLANT

Figure 1:
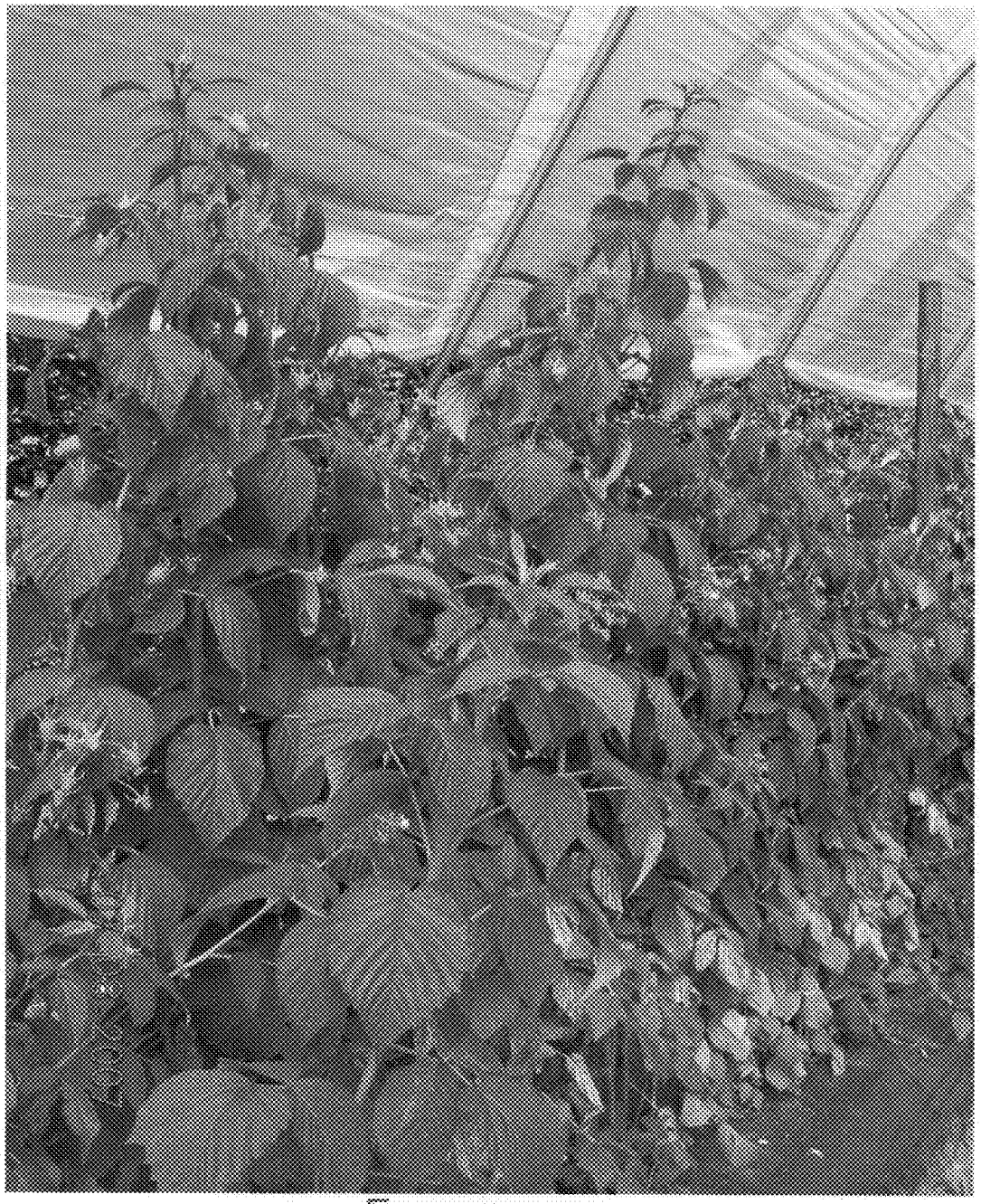
FIG. 1: Plant habit and foliage of 'Autumn Treasure' growing under polythene tunnels.
Figure 2:
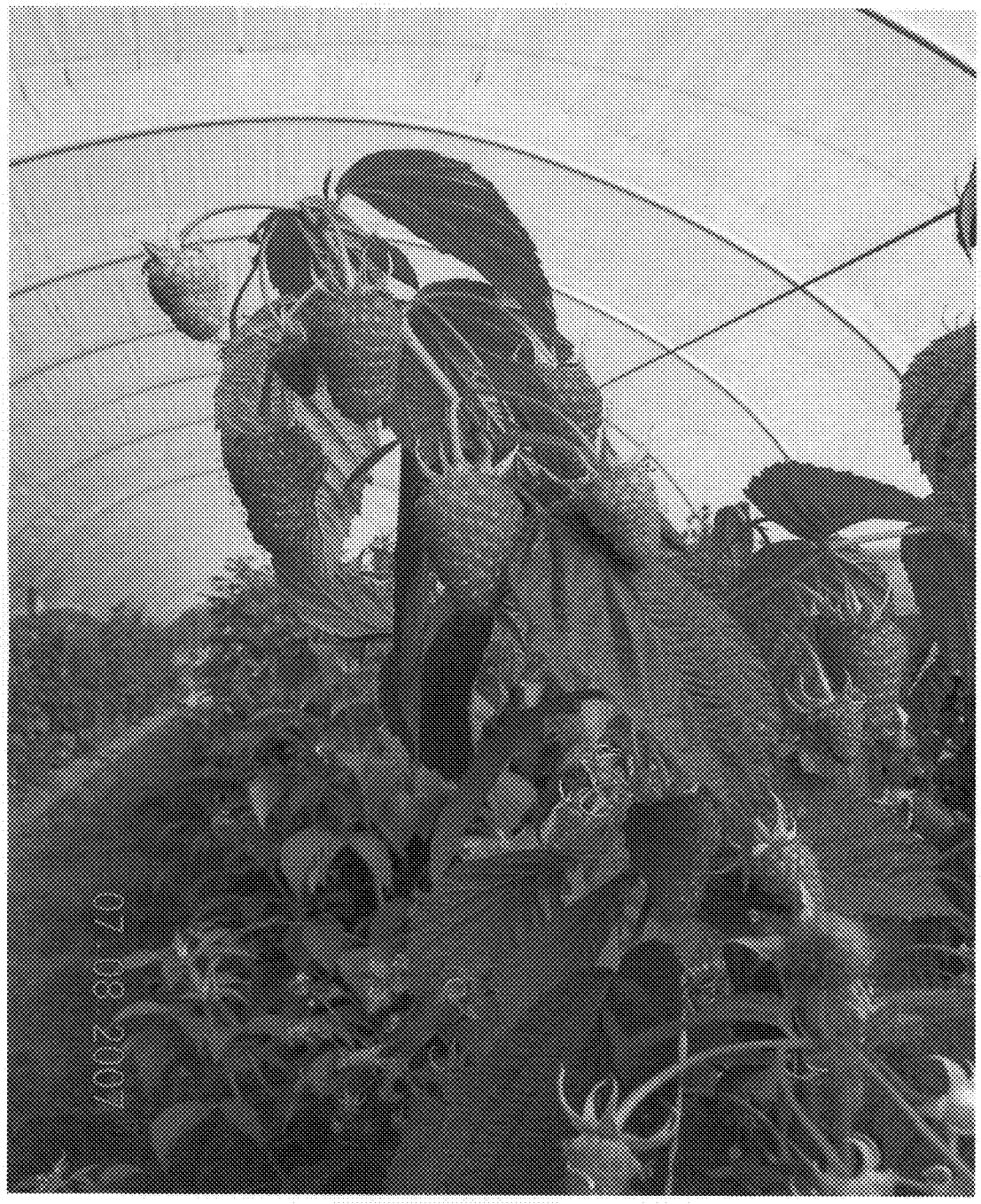
FIG. 2: Cane tips and fruit of 'Autumn Treasure' growing under polythene tunnels.

The chart used in the identification of colour is that of The Royal Horticultural Society (R.H.S. Colour Chart). The description is based on the observation of specimens of the new cultivar growing under a polythene tunnel in Kent (UK) in 2007 and using nomenclature in agreement with Leemans and Nannenga 1957 "A morphological classification of raspberry varieties" IVT, Wageningen as well as Krüssmann 1984 Timber Press, London.

Botanical classification: *Rubus idaeus l.*

General plant characteristics: The new cultivar is being grown for its primocane fruit crop. The primocanes are reasonably vigorous, erect and pale green in colour (Yellow-Green 145B) presenting variable amounts of red pigment (43B) depending on the conditions of cultivation and darkening as the season progresses. If retained, the floricanes are typically grey-brown (N199C). It produces a moderate number of current season shoots, around 90% of which bear fruit. Typical fruiting primocanes are, on average, approximately 1.53 m high and 9.9 cm in diameter (at 0.5 m from the ground). The number of fruiting laterals per primocane typically varies from 14 to 17; equivalent to 36% to 50% of the length of the primocane. In the floricanes, a typical lateral (developed from a bud between 50 and 70 cm from the ground) measures on average 23 cm in length and 3.6 mm in diameter at 10 cm from the base producing between 9 and 13 flowers (10 on average) and has a color (145B). Spines are absent on all plant parts. 'Autumn Treasure' has a vigorous root system and propagates readily.

Foliage: The composite leaves present three sessile non-overlapping leaflets with a double serrated edge and regular plication. The pose of the leaflets is pendant to bulging. Typical terminal leaflets are approximately 13.0 cm in length and 9.3 cm in width (1.4 ratio) presenting a cuspidate apex and a shallow cordate base. Typical lower leaflets are approximately 10.1 cm in length and 5.9 cm in width (1.7 ratio) presenting a cuspidate apex and an obtuse base. The leaves commonly are Green Group 137A on the upper side and Grey-Green Group 191B or 194A on the under side. Typical petioles show a Yellow-Green Group 146D colouration where blush is absent and are long and slender (62 mm on average but ranging from 51 mm to 72 mm) with an average diameter of 2 mm).

Flowering in the floricane commonly starts from late April to early May (25$^{th}$ April to 8$^{th}$ May) and continues for 4 weeks approximately in SE England whilst primocanes typically start flowering around the third week of June and continues through September in Kent (UK). Flower buds are conical measuring on average 131.2 mm in length by 74.4 mm in diameter (average ratio 0.57) just before opening. They are smooth and very pale green (Yellow-Green 147C) with frequent areas of reddish blush (Greyed-Purple 185B). Pedicels are smooth and can show red pigmentation on the upper side (Greyed-Purple 185B) remaining green on the under side (Yellow-Green 147B); their length can vary between 111 mm and 371 mm (255 mm average) depending on the position of the bud/flower on the lateral. The flowers present five petals (average dimensions: 30.8 mm in width by 73.6 mm in length, 0.42 ratio, oval in shape, margin entire, apex rounded, base rounded, texture smooth) and five sepals (average dimensions: 45.6 mm in width by 130.8 mm in length, 0.36 ratio, shape lanceolate, apex acute, texture smooth, margin entire, color 138B both surfaces); the number of styles can vary between 74 and 97 (83.8 on average) with an average length of 90.6 mm; the number of stamens varies between 88 and 99 (93.6 on average). The petals are pure white, White Group 155B to 155D. The diameter of a fully opened flower measured to the tips of opposing sepals is 23.4 mm on average. The flowers produce copious pale yellow pollen (5B).

Fruiting season: Fruit mainly is borne on the current season's canes similar to that of the cultivars 'Autumn Bliss' (U.S. Plant Pat. No. 6,597) and 'Heritage' (unpatented). The primocane fruiting in Kent (UK) can be defined as mid-season. In a typical year the fruit starts to ripen at the end of July but significant yields are not achieved until the middle of August. It reaches 50% pick date in late August to early September, 10 to 14 days later than 'Autumn Bliss' (U.S. Plant Pat. No. 6,597). Yield starts to decline towards the end of September but some later canes will continue fruiting well into October.

Fruit characteristics: Typical berries are conical to long conical, 23 mm long and 18 mm wide (1.3 ratio) on average. Fruit colour ranges from Red Group 47A at early maturity to Grey-Red Group 180A or 182A at full maturity, lighter than that of 'Autumn Bliss' (U.S. Plant Pat. No. 6,597) and of similar brightness. Berries show a moderate adherence to the receptacle and can be easily plugged by the pickers. The plug is long conical, composed of 72 to 79 drupelets slightly rough on the surface and of Yellow Group 10D colour. Individual drupelets are small and give the berry an attractive outline. The fruit is firmer and has better post-harvest storage performance than 'Autumn Bliss' (U.S. Plant Pat. No. 6,597). Mean berry weight is approximately 4.6 g with a soluble solids content (Brix) of 10.4% on average. Seeds weigh approximately 1.8 mg on average. Since the new cultivar is being grown for its primocane fruit crop, characteristics of the over-wintered floricanes have not been recorded nor has their fruit production evaluated. The typical primocane crop in Kent (UK), one year after planting is higher than that of 'Autumn Bliss' (U.S. Plant Pat. No. 6,597) and of 'Polka' (unpatented cultivar).

Pests and disease resistance: 'Autumn Treasure' is resistant to biotypes 1–4 of the large raspberry aphid (*Amphorophora idaei*), the European vector of the raspberry mosaic virus complex, and despite field exposure has remained free of raspberry bushy dwarf virus (RBDV) to date. It has been highly resistant to root rot (*Phytophthora fragariae* var. *rubi*) in glass house inoculated pot tests. The new cultivar showed much higher tolerance than other cultivars to wilt (*Verticillium dahliae*) in glass house pot tests in 2007 and no symptoms of *Verticillium* wilt have been detected in the field.

Market potential: The berries are suitable for the commercial production of high quality fresh berries for shipping. It is also amenable to low input or organic systems as well Pick-Your-Own (U-Pick) farms and amateur growers.

Figure 3:
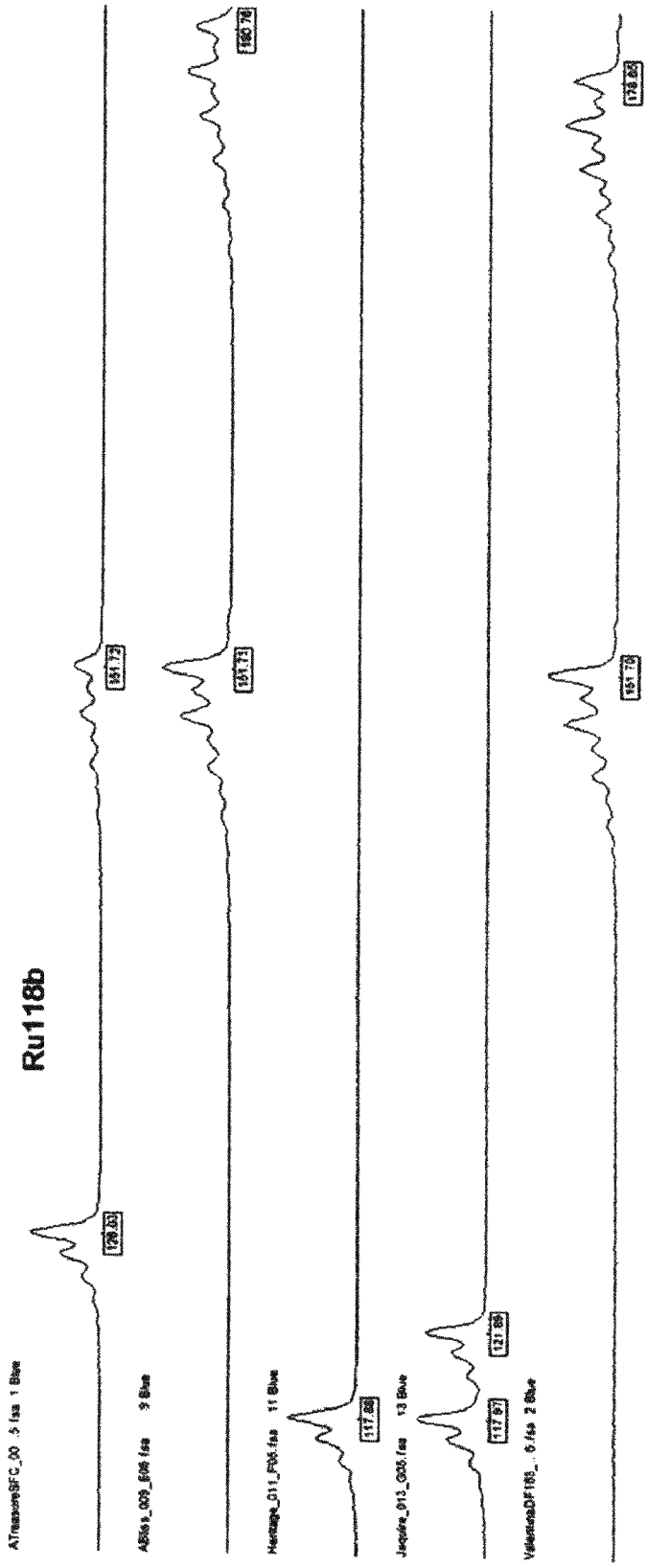
FIG. 3: SSR marker Ru118b showing polymorphism in raspberry cultivars. Traces, from top to bottom, correspond to 'Autumn Treasure', 'Autumn Bliss', 'Heritage', 'Joan Squire' and 'Valentina'. Traces obtained using fluorescently label PCR primers visualized in an ABI 3100 Genetic Analyzer.

Genetic fingerprinting: Genetic fingerprinting, also known as DNA profiling, allows individuals from the same species to be distinguished using samples of their DNA (Deoxyribonucleic acid). A variety of laboratory techniques can be used to detect distinctive patterns of polymorphism in the samples. Microsatellites, also know as Simple Sequence Repeats (SSRs) or Short Tandem Repeats (STRs), are one of the most commonly used markers for genetic fingerprinting. SSRs are short repeated sequences of DNA. The number of repeats varies between individuals creating polymorphic regions that can be revealed using Polymerase Chain Reaction (PCR) to copy the sample-DNA thousands of times thus allowing the visualisation of the polymorphism. Genetic analysis of 'Autumn Treasure', using specific SSR markers published for red raspberry (Graham J, Smith K, Woodhead M, Russell J: Development and use of simple sequence repeat SSR markers in *Rubus* species. Molecular Ecology Notes 2002, 2:250–252.), produced unique DNA patterns different from those of 'Autumn Bliss' (U.S. Plant Pat. No. 6,597), 'Joan Squire' (unpatented cultivar), 'Heritage' (unpatented cultivar) and 'Valentina' (unpatented cultivar). (FIG. 3)

The invention claimed is:

1. A new and distinct variety of Raspberry plant named 'Autumn Treasure' as described and illustrated.

* * * * *